United States Patent [19]

Welker

[11] 4,346,611
[45] Aug. 31, 1982

[54] INSERTION REGULATOR FOR PRESSURIZED PIPELINES

[76] Inventor: Robert H. Welker, 13839 W. Belfort, Sugar Land, Tex. 77478

[21] Appl. No.: 218,112

[22] Filed: Dec. 19, 1980

[51] Int. Cl.³ ............................................ G01N 1/14
[52] U.S. Cl. ............................... 73/863.86; 73/432 R
[58] Field of Search ............... 73/86, 432 R, 863.82, 73/863.86

[56] References Cited

U.S. PATENT DOCUMENTS

| | | | |
|---|---|---|---|
| 2,623,544 | 12/1952 | Waters et al. | 73/863.86 |
| 2,870,629 | 1/1959 | Willis | 73/86 |
| 3,007,340 | 11/1961 | Kraftson | 73/432 |
| 3,718,034 | 2/1973 | Swearingen | 73/86 |
| 3,812,722 | 5/1974 | Soudelier | 73/863.82 |
| 4,177,676 | 12/1979 | Welker | 73/432 |

*Primary Examiner*—Herbert Goldstein
*Attorney, Agent, or Firm*—Gunn, Lee & Jackson

[57] ABSTRACT

An insertion regulator for insertion into and retraction from a pressurized pipeline and the like includes a sensor probe housing structure that is adapted for sealed connection at an aperture formed in the pipeline. The probe housing defines a probe receptacle opening into the pipeline. A sensor probe extends through the probe housing with an inner portion thereof in communication with the pressurized fluid medium within the pipeline. The inner extremity of the sensor probe is inserted into the pipeline against the influence of pressure contained therein by means of an actuator system employing a piston actuator that is movable responsive to pressure communicated thereto from the pipeline. The inner extremity of the probe is positionable at a preselected position within the pipeline for optimum sample taking and is retractable to a protected, noninterfering position within the probe receptacle to permit the passage of pigs and other objects through the pipeline.

13 Claims, 2 Drawing Figures

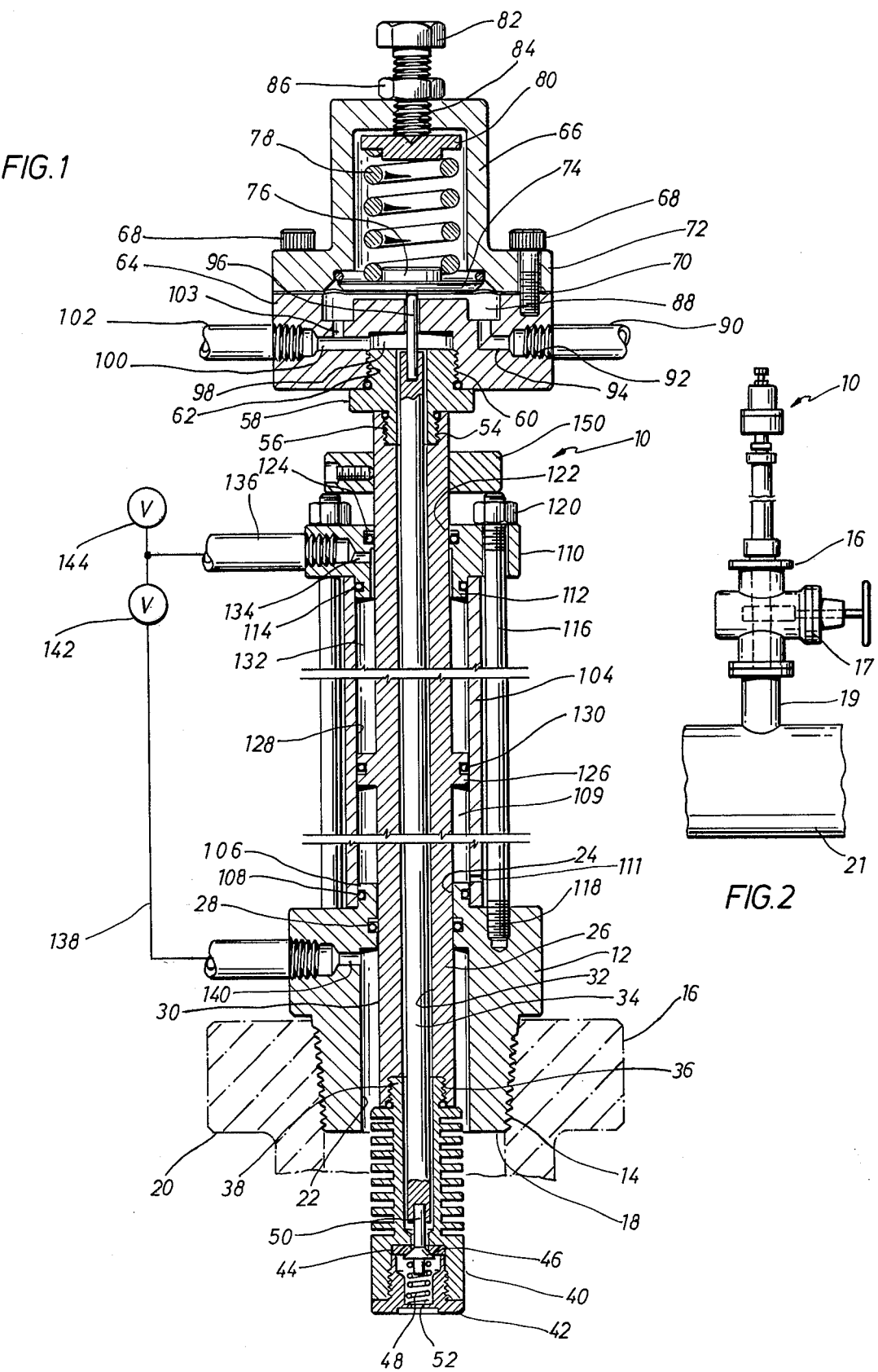

# 4,346,611

INSERTION REGULATOR FOR PRESSURIZED PIPELINES

FIELD OF THE INVENTION

This invention is directed generally to insertion regulators that are positioned within pipelines, pressurized vessels and the like for the purpose of sample taking and to operating pneumatic controllers, pumps valve operators or other instruments that require a continuous pressure. More specifically, the present invention is directed to an insertion regulator mechanism that is capable of being inserted into a pipeline or vessel to a preselected position for optimum sample taking and, in the case of pipelines, to permit objects such as pigs, spheres and the like to pass through the pipeline, is movable to a retracted, protected position within a receptacle defined by the apparatus.

BACKGROUND OF THE INVENTION

This invention relates to the subject matter covered in U.S. Pat. No. 4,177,676; of common inventorship herewith. Instrument regulator systems or sensors are typically interconnected with pipelines, pressure vessels and the like for the purpose of sample taking within the vessel. Heretofore, various instrument regulator systems have been employed in pipelines, pressure vessels and the like for the purpose of establishing process interconnection with various instruments such as calorimeters, gravitometers, hydrogen sulfide analyzers and the like. Ordinarily, instrument regulator systems are mounted externally of pipelines, pressure vessels and the like and are communicated with the pressurized fluid therein by means of a suitable passage. Although most instrument regulators are so mounted, the samples that are taken can be in error because they are not taken directly from the pipeline or pressure vessel. In one known case, an instrument regulator has been employed which is interconnected with a pipeline structure in such a manner that an inner portion thereof extends to a position within the pipeline to enable optimum sample taking. A primary problem with instrument regulators is the fact that the pipeline may not be cleaned with internal pipeline scrapers and objects such as pigs, spheres and the like may not pass through the pipeline without first removing the instrument regulator from the pipeline. This problem is also addressed in U.S. Pat. No. 4,177,676. It is desirable, therefore, to provide an instrument regulator system wherein the sample taking probe is adapted for positioning at an optimum sample taking position within the pipeline and, is retractable from the pipeline in order to allow the passage of scrapers, pigs, spheres the other pipeline service equipment through the pipeline.

In many cases, it is desirable that an instrument regulator be capable of removal from the pipeline while the pipeline is maintained under pressure. For example, removal of instrument regulators under pressure is accomplished to facilitate running of pigs through the pipeline and to do simple maintenance on the regulator system without blowing down the pipeline. Installation and removal of instrument regulators and other such sensors while a pipeline is maintained under pressure is also important. For example, it may be desirable to facilitate installation of instrument regulator through a "hot tap" into a section of pipeline that cannot be blown down. The instrument servicing operations may be carried out without necessitating shutting down of the flow system or process, thereby saving the production losses that would otherwise result.

SUMMARY OF THE INVENTION

It is a primary feature of the present invention to provide a novel instrument regulator system incorporating a sample taking probe that may be selectively moved from an operative position within the pipeline to a retracted position where the sample taking extremity of the probe is retracted into a protective receptacle located outside of the cylindrical, internal surface of the pipeline.

It is also a feature of this invention to provide a novel instrument regulator system having a movable probe that is capable of being inserted into a pipeline for sample taking against the pressure of the pipeline.

It is an even further feature of this invention to provide a novel instrument regulator system having a movable probe that is also capable of being retracted from the pipeline to a protected position while the pipeline is maintained under full pressure and operating characteristics.

Among the several features of this invention is contemplated the provision of a novel instrument regulator system having a movable probe mechanism that is selectively movable to operative and retracted positions by means of a fluid pressure energized system that is energized by the pressure contained within the pipeline.

Briefly, the present invention is directed to an automatic insertion regulator mechanism having sensor such as a sample taking probe structure that is capable of being inserted into and retracted from a pressurized pipeline or other pressure vessel. The instrument regulator incorporates a probe housing structure that is adapted for sealed connection to the pipeline. The inner portion of the probe housing defines a protective receptacle that is open to pressure from the pipeline. A pressure regulator probe extends through the probe housing or support base structure and through the protective receptacle, with an inner, sample taking portion of the probe adapted to be positioned at an optimum sample taking position within the pipeline.

A fluid energized actuator system is coupled to the probe mechanism and incorporates a piston assembly, disposed within a cylinder and which cooperates with the cylinder to define a variable volume actuator chamber. The piston may be an integral enlarged structure defined on the actuator shaft and, being of larger diameter than the actuator shaft, represents a piston area that is greater than the area represented by the cross-section dimension of the actuator stem. Pressure on one side of the piston acts on these respective cross-sectional dimensions and develops a resultant force that urges the piston and the actuator shaft in one axial direction. The actuator chamber is in fluid communication with pressure from the pipeline by a pressure supply line that is controlled by an insertion control valve which is opened to allow introduction of pipeline pressure into the variable volume chamber. The pressure of the line fluid acts on the annular piston of the actuator system and forces the piston and probe insertion shaft inwardly thereby positioning the inner extremity of the probe at the proper position within the pipeline. The variable volume chamber is also communicated with a block valve to block communication of pressure to the piston and a vent or blow-down valve that is capable of relieving pressure from the piston chamber. At some point during blow-down of the piston cylinder, pressure within the pipeline, acting on the lower portion of the actuator shaft, will overcome the dissipating resultant force acting on the piston. When this occurs, pressure within the pipeline will induce a force to the probe mechanism that moves the probe outwardly and moves the inner extremity of the probe outside of the flow passage of the pipeline and into the protective receptacle. In its protected position within the protective receptacle, it is not possible for the probe to interfere with movement of pigs, scrapers and the like through the pipeline. In the operative position thereof, the probe is positioned within the pipeline and thus within the flow stream for optimum sample taking.

The instrument regulator system incorporates an inlet valve that is positioned at the inner extremity of the sample taking probe. The inlet valve is selectively opened and closed by means of a valve actuator shaft and extends through the probe and is operated by selective pressure energization of a spring controlled diaphragm or piston assembly.

BRIEF DESCRIPTION OF THE DRAWINGS

In order that the manner in which the above recited advantages and objects of this invention are attained and can be understood in detail, more particular description of the invention, briefly summarized above, may be had by reference to the specific embodiment thereof that is illustrated in the appended drawings, which drawings form a part of this specification. It is to be understood, however, that the appended drawings illustrate only a typical embodiment of the invention and, therefore, are not to be considered limiting of its scope, for the invention may admit to other equally effective embodiments.

In the Drawings

FIG. 1 of the drawings is a sectional view of an instrument regulator mechanism constructed in accordance with the present invention and shown to be connected to a full open type valve that is connected to the wall structure of a pipeline or pressure vessel that is shown in broken line.

FIG. 2 is a side elevational view illustrating connection of the apparatus of FIG. 1 to a pipeline structure.

DETAILED DESCRIPTION OF PREFERRED EMBODIMENT

Referring now to the drawings, an automatic insertion instrument regulator is illustrated generally at 10 and is connected to a pipeline structure in the manner illustrated in FIG. 2. A branch conduit 19 is welded or otherwise affixed to the pipeline and is provided with a flange for bolted connection of a valve 17 in assembly with the branch conduit. The valve 17 may be of any suitable positive closing type having a straight through bore through which an instrument probe will pass. The opposite connection flange 16 of the valve 17 receives the automatic instrument regulator mechanism of this invention in any suitable manner. As shown in FIG. 1, the instrument regulator mechanism is threaded into the flange, but, if desired, may be bolted or otherwise assembled to the valve 17. The instrument regulator incorporates a lower housing or base structure 12 that is formed to define an externally threaded lower extremity 14 that is capable of being threaded into sealed engagement with a full open block valve that is connected by any suitable means to a pipeline 16 or the wall structure of any suitable pressure vessel. Although the base structure 12 is shown to be designed for threaded engagement with the wall structure of the valve 16, it is not intended to limit the present invention to such a threaded engagement. It is within the scope of this invention to provide flanged connection of the base 12 to a conduit that may be isolated by a valve in connection with the wall structure of the valve or to provide any other suitable system for sealed interconnection of the base structure to the valve. The base portion 12 of the instrument regulator 10 is formed to define an internal receptacle 22 that opens into the flow passage of a valve 16 that is connected to the pipeline and also forms a centrally oriented passage 24 through which a probe insertion shaft 26 extends. An annular seal assembly 28 is received within an annular seal groove defined within the base structure 12 and establishes sealed engagement with respect to the outer cylindrical surface 30 of the probe insertion shaft 26.

The probe insertion shaft 26 is of tubular form defining an elongated internal passage 32 through which an inlet valve actuator shaft 34 extends. The lower or inner extremity of the probe insertion shaft 26 is formed to define an internally threaded receptacle 36 that receives an externally threaded outer connector portion 38 of an inlet valve housing structure 40. The lower or inner extremity of the inlet valve housing 40 is defined by means of a retainer structure 42 that is threadably received within the valve housing and functions to retain an annular valve seat 44 in properly seated relation within a valve receptacle. An inlet valve 46, which is a poppet valve, defines a generally conical sealing surface that is adapted to engage a mating, frusto-conical sealing surface defined by the valve seat 44. The valve seat 44 is composed of any suitable sealing material within the spirit and scope of this invention. For example, the seat element 44 may be composed of polytetrafluoroethylene or any one of a number of other suitable plastic sealing materials. Other seat materials may be employed as well. The poppet valve 46 is urged against the valve seat 44 by means of a compression spring 48 that is also retained within the valve receptacle by means of the retainer element 42. The inlet valve further incorporates a valve actuator stem 50 having an outer extremity thereof received within an appropriate receptacle defined in the inner extremity of the valve actuator shaft 34. As the valve actuactor shaft 34 is moved inwardly or downwardly, it acts against the valve stem 50, thereby moving the inlet poppet valve 46 downwardly against the force of the compression spring 48. When the poppet valve is unseated, fluid adjacent to the valve housing enters the valve chamber through inlet openings 52 and flows past the poppet valve into the elongated passage 32 of the probe insertion shaft 26. The valve actuator shaft 34 defines a loose fit within the elongated passage 32 of the probe insertion shaft, thereby defining an annulus between the shaft and passage that serves as an outward flow path for pressurized fluid flowing past the open inlet poppet valve 46.

At the upper extremity of the probe insertion shaft 26, there is provided an internally threaded receptacle 54 that receives the externally threaded inner extremity 56 of a housing connector adapter 58. The upper extremity of the housing connector adapter is formed to define external threads as shown at 60 which are received by an internally threaded lower portion 62 of a housing base 64. A spring housing structure 66 is connected to the housing base 64 by means of a plurality of cap screws or bolts 68. A diaphragm 70 has the outer peripheral portion thereof entrapped between the housing base 64 and a bolt flange portion 72 of the spring housing 66. A diaphragm plate 74 is positioned at the lower portion of the spring housing 66 in contact with the diaphragm 70 and incorporates a spring guide 76 that receives the lower extremity of a range spring 78. A spring guide structure 80 is adapted to be received by the upper extremity of the range spring and is positioned against an adjusting screw or bolt 82 that extends through a threaded aperture 84 formed in the upper portion of the housing. A lock nut 86 is received by the adjustment screw 82 and functions to lock the adjustment screw in any suitable position relative to the spring housing 66. The purpose of the adjustment nut 82 is to establish the compressive loading of the range spring 78 against the diaphragm plate 74 and diaphragm 70 to regulate the pressure at which the poppet valve 46 opens. Immediately below the diaphragm 70, the housing base structure 64 is formed to define an annular diaphragm chamber 88 having communication with a conduit shown schematially at 90 which is reeived by the threaded inlet portion 92 of a passage 94 formed in the base 64. A relief valve or/and a pressure gauge may be connected to conduit 90 for relieving and sensing of pressure within the chamber 88.

The valve actuator shaft 34 is formed to define a receptacle at the upper extremity thereof that receives a pin 96 having its upper extremity in engagement with the diaphragm 70. As the diaphragm 70 is moved downwardly under the influence of the range spring 78, acting through the diaphragm plate 74, the pin 96 is moved downwardly, also moving the valve control shaft downwardly and thus opening the poppet valve 46.

Fluid pressure flowing past the poppet valve 46 and upwardly or outwardly through the annulus between the shaft 34 and the passage 32 enters an oulet chamber 98 and flows through and outlet passage 100 to a suitable outlet conduit illustrated schematically at 102. A pressure sensing port 103 communicates the passage 100 with the diaphragm chamber 88, allowing diaphragm control to be achieved through conduit 102. By controlling the pressure within the diaphragm chamber 88, pressure acting against the diaphragm 70 urges the diaphragm plate 74 upwardly causing the range spring 78 to be compressed. Upward movement of the diaphragm, in this manner, allows the compression spring 48 of the poppet valve 46 to urge the poppet valve upwardly to the closed position thereof. Conversely, as the pressure within the diaphragm chamber 88 is depleted, the range spring 78 urges the diaphragm plate and diaphragm downwardly, thereby acting against the pin 96 and forcing the valve operating shaft 34 downwardly to open the inlet poppet valve. When this occurs, a sample flows past the poppet valve and outwardly through the outlet conduit 102 in the manner described above.

As mentioned above, it is desirable to cause linear movement of the sampling probe into the pipeline, thus positioning the inlet portion of the probe at the proper position for sampling within the pipeline. Under circumstances where pigs or other such devices are to be passed through the pipeline, it is desirable to insure retraction of the probe structure out of the flow passage of the pipeline and into a protective receptacle provided therefor. It is desirable, therefore, to provide a probe actuator mechanism having the capability of inserting or retracting the probe as desired. In accordance with the present invention, a mechanism for controllably inserting and retracting the sampling probe may conveniently take the form illustrated in the drawing. A probe actuator cylinder is provided as shown at 104 having the lower extremity thereof received by an axially extending boss 106 and is aligned with respect to the boss 106 by means of an annular resilient element 108 such as an O-ring or the like which accommodates manufacturing tolerances between the boss and the cylinder. A lower variable volume chamber 109, beneath the piston is vented by means of a port 111 formed in the cylinder to prevent pressure interference with piston travel. At the upper extremity of the probe actuator cylinder 104 is provided a cylinder closure cap 110 having an axially extending flange portion 112 that is received within the upper extremity of the cylinder and sealed therewith by means of an annular sealing element 114 such as an O-ring or the like. The cylinder closure cap 110 is secured in assembly with the cylinder 104 by means of a plurality of tie bolts 116 having lower portions thereof received within threaded openings 118 defined in the base structure 12. Nuts 120 that are attached to the tie bolts function to force the cylinder closure cap 110 into tightly secured relation with the cylinder 104 and also function to force the cylinder into tightly received relation with respect to the base structure 12 of the instrument regulator. The probe insertion shaft 26 extends through an aperture 122 of the cylinder closure cap 110 and is sealed with respect to the closure cap by means of an annular sealing element 124.

An annular enlargement 126 is provided on the probe insertion shaft intermediate the extremities thereof and functions as a piston. The piston 126 is sealed with respect to the internal cylindrical surface 128 of the actuator cylinder 104 by means of an O-ring 130 or any other suitable sealing element. The piston 126 cooperates with the cylinder structure 104 to define a variable volume chamber 132 that communicates with a passage 134. A conduit 136 is received within a threaded portion of the passage 134 and functions to communicate fluid pressure to and from the variable volume chamber. A conduit 138 is coupled with the base portion 12 of the instrument regulator and is communicated by a passage 140 with the protective receptacle 122, thus pressurizing the conduit 138 in accordance with the pressure of the fluid medium being controlled by the pipeline 16. The conduit 138 is provided with an injection valve 142 that may be opened to introduce line pressure from the pipeline through the conduit 136 and passage 134 into the variable volume chamber 132. When this occurs, fluid pressure acts upon the upper portion of the piston 130, developing a downwardly acting force on the piston and probe insertion shaft. The probe insertion shaft defines a cross-sectional area at the seal 28 which is acted upon the pressure of the fluid medium within the pipeline, thereby developing an upwardly or outwardly directed force on the probe insertion shaft. Since the cross-sectional area of the piston 126 is greater than the cross-sectional area defined by the shaft 26 at the seal 28, a resultant force is developed, acting downwardly on the probe insertion shaft which causes the shaft 26 to move downwardly, thus positioning the sampling probe portion thereof within the pipeline at the preselected position for sampling.

The conduit 136 tees into the conduit 138 between the insertion valve 142 and pressure relief valve 144. With valve 142 closed and pressure relief valve 144 open, fluid pressure within the variable volume chamber 132 is open to the atmosphere or to any other suitable receiver. The pressurized fluid within the pipeline, acting upon the probe insertion shaft, forces the shaft upwardly, thereby moving the piston and probe upwardly and retracting the probe within the protective receptacle 22. Thus, the sampling probe may be inserted into the pipeline or retracted within the protective receptacle simply by appropriate manipulation of the insertion valve 142 and the pressure relief valve 144. In both cases, line pressure is utilized to position the probe and, therefore, an auxilliary pressure control system is not required.

While the foregoing is directed to the preferred embodiment of the present invention, other and further embodiments of the invention may be devised without departing from the basic concept thereof, and the scope thereof is determined by the claims which follow.

I claim:

1. An apparatus for mounting a sensor means for insertion into and retraction from a pressurized vessel such as a pipeline, said apparatus comprising:
  a. sensor probe mounting means adapted for sealed connection to said pipeline, said probe mounting means defining sensor probe receptacle means;
  b. an elongated sensor probe shaft of tubular from defining an elongated passage, said probe shaft extending in relatively movable sealed relation through said sensor probe mounting means and defining inner and outer extremities, said sensor probe shaft being movable to an operative position where said inner extremity is positioned within said pipeline and movable to a retracted position where said inner extremity is retracted from said pipeline and positioned within said sensor probe receptacle means; and
  c. an inlet valve being provided at the inner extremity of said sensor probe shaft;
  d. a valve actuator shaft being movably disposed within said elongated passage and having operative connection with said inlet valve;
  e. a diaphragm assembly being connected to the outer extremity of said sensor probe shaft and having actuating connection with one extremity of said valve actuator shaft;
  f. means controlling actuation of said diaphragm assembly for inducing inlet valve opening movement to said diaphragm assembly and valve actuator shaft;
  g. a sensor probe being located at said inner extremity of said sensor probe shaft; and
  h. fluid pressure energized actuator means being controllably coupled with said sensor probe shaft and being controllably energized by fluid pressure from said pipeline to ensure insertion movement of said probe from said receptacle to a preselected position within said pipeline, upon deenergization of said actuator means said probe shaft and sensor probe being moved to said retracted position by fluid pressure within said pipeline.

2. An apparatus as recited in claim 1, wherein said actuator means comprises:
  a. an elongate cylinder;
  b. piston means extending from said sensor probe shaft and being located within said elongate cylinder, said piston means cooperating with said cylinder to define a variable volume chamber;
  c. means selectively communicating said variable volume chamber with said fluid pressure of said pipeline and causing selective application of said fluid pressure to said piston means for moving said piston means and said sensor probe to said operative position; and
  d. means selectively venting fluid pressure from said variable volume chamber to relieve fluid pressure therein from acting on said piston means and allowing pressure within said pipeline to move said sensor probe to said retracted position.

3. The apparatus of claim 1, wherein:
  (a) said sensor probe cooperates with said probe shaft mounting means to define a first cross-sectional area continuously exposed to the pressurized fluid medium within said pipeline; and
  (b) said piston means defines a second cross-sectional area that is selectively exposed to the pressurized fluid medium within said pipeline, said second cross-sectional area being greater than said first cross-sectional area and pressure acting simultaneously on said first and second cross-sectional areas developing a resultant force on said piston and sensor probe acting to move said sensor probe toward said operative position thereof.

4. The apparatus of claim 1, wherein said diaphragm assembly comprises:
  (a) a diaphragm housing defining a control pressure inlet and sample outlet;
  (b) diaphragm means disposed in sealed relation within said diaphragm housing and cooperating therewith to define a pressure chamber, said diaphragm means having operative engagement with said valve actuating shaft;
  (c) means communicating control pressure to said control pressure inlet to maintain said inlet valve closed; and
  (d) spring means imparting a force to said diaphragm in opposition to said control pressure, upon relief of said control pressure said spring means imparting valve opening movement to said diaphragm, said valve actuator shaft and valve to conduct a specimen from said pipeline to said sample outlet.

5. The apparatus of claim 1, wherein said sensor probe mounting means comprises:
  a support base defining connection means for sealed attachment to conduit means extending to said pipeline; said sensor probe receptacle means being defined by said support base and opening toward said pipeline at said inner extremity of said support base.

6. The apparatus of claim 5, wherein said sensor probe mounting means further comprises:
  (a) passage means communicating said sensor probe receptacle with said fluid pressure actuator means; and
  (b) pressure control valve means controlling said passage means and thus selectively controlling application of fluid pressure from said pipeline to said fluid pressure energized actuator means.

7. The apparatus of claim 6, including:
  vent valve means interconnected with said passage means and being selectively opened to vent pressure from said actuator means, said pressure control valve and said vent valve being adapted for operation such that one of said valves is open and the other of said valves is closed.

8. The apparatus of claim 1, including:
  means selectively limiting insertion movement of said sensor probe into said pipeline and selectively positioning said sensor probe within said pipeline at said operative position thereof.

9. An apparatus of claim 1, wherein said actuator means comprises:
(a) an elongate cylinder being interconnected with said support base and receiving said sensor probe shaft in movable relation therein;
(b) a piston being connected to said probe shaft and having an outer periphery in sealed movable engagement with said cylinder, said piston defining a first pressure responsive area; and
(c) seal means establishing said sealed relation of said sensor probe shaft with respect to said sensor probe mounting means and cooperating with said sensor probe shaft to define a second pressure responsive area of said probe shaft being of such dimension relative to the dimension of said first pressure responsive area that application of common pressure to said first and second pressure responsive areas develops a resultant force urging said piston and sensor probe shaft toward said pipeline.

10. An apparatus of claim 9, wherein:
said first pressure responsive area is greater than said second pressure responsive area.

11. An apparatus of claim 9, wherein:
(a) said piston cooperates with said cylinder to define a variable volume pressure chamber within said cylinder;
(b) passage means communicates said variable volume chamber with the pressure of said pipeline; and
(c) valve means controls introduction of pressure from said pipeline to said variable volume chamber and venting of pressure from said variable volume chamber.

12. An apparatus of claim 11, wherein said valve means comprises:
(a) block valve means supporting said sensor probe mounting means and being capable of closing and isolating said variable volume chamber from the pressure of said pipeline; and
(b) vent valve means capable of opening to vent pressure from said variable volume chamber.

13. An apparatus of claim 9, including:
means for establishing a lower pressure acting upon said first pressure responsive area as compared to pressure acting upon said second pressure responsive area and developing a resultant force urging said sensor probe shaft away from said pipeline and toward said retracted position.

* * * * *